United States Patent [19]

Smith

[11] 3,956,925
[45] May 18, 1976

[54] HARDNESS TESTER
[76] Inventor: Samuel C. Smith, 210 Hartman Road, Newton, Mass. 02159
[22] Filed: Dec. 30, 1974
[21] Appl. No.: 537,244

[52] U.S. Cl. ................................................. 73/81
[51] Int. Cl.² .......................................... G01N 3/42
[58] Field of Search ..................... 73/81, 83, 150 R

[56] References Cited
UNITED STATES PATENTS

| | | | |
|---|---|---|---|
| 1,870,415 | 8/1932 | Lewis | 73/81 |
| 2,422,634 | 6/1947 | Riepert et al. | 73/81 |
| 2,643,545 | 6/1953 | More | 73/83 |
| 2,914,937 | 12/1959 | More | 73/81 |
| 3,524,343 | 8/1970 | Sear | 73/83 |
| 3,877,297 | 4/1975 | Oesterle | 73/81 |

*Primary Examiner*—James J. Gill
*Attorney, Agent, or Firm*—Thompson, Birch, Gauthier & Samuels

[57] ABSTRACT

This invention relates to a method and a portable apparatus for testing the hardness of thin film plastics. The basic apparatus comprises a base stand including a platform for the sample to be tested, an indenter consisting of a pointed shaft in conjunction with a weight, and a dial gauge.

7 Claims, 3 Drawing Figures

HARDNESS TESTER

BACKGROUND OF INVENTION

A large variety of hardness testers for measuring the hardness of solid materials are known in the art. The typical hardness tester comprises some type of indenter (which may be pointed or rounded depending on the particular intended application), a means of applying a driving force to the indenter, and a means for measuring the amount of penetration of the material being tested. Typical of such testers are U.S. Pat. Nos. 2,544,205; 2,663,185; and 3,182,491.

Somewhat special problems are presented by softer, elastic materials; and, in general, a hardness tester adapted to measuring the hardness of metals, ceramics and the like will not perform well with plastics. Several techniques, however, have been developed for testing the hardness of plastic-like materials as shown in U.S. Pat. Nos. 2,373,662; 3,406,566; 3,597,965; and 2,892,342. All of these references deal with testing the hardness of bulk materials and not with thin plastic films and the special requirements thereof.

Polymer plastic coatings are presently employed in a seemingly endless variety of protective and decorative applications. Although plastics have demonstrated a durability unparalleled by conventional wood and metal products, they are subject to gradual degradation under the influence of time, normal weathering, heat, cold, stress and strain, exposure to certain chemicals, ultraviolet light and other forms of radiation energy, and perhaps many other factors that have yet to be discovered. It will be appreciated that the rate at which such degradation occurs also varies according to the chemical structure of the plastic. The visible effects of such degradation include discoloration, warping, cracking and similar signs of brittleness, but only in the advanced stages of the degradation. Another common type of plastic deterioration is known as hydrolytic stability failure. Hydrolytic stability failure (sometimes called reversion) refers to the quality of a material which, having cured to a solid state from its original liquid state, can revert to the liquid state or soften considerably. There is a prescribed MIL SPEC for hydrolytic stability tests but it does not include coatings and thin film materials. Under particularly severe operating conditions, for example in protective applications in the aerospace industry, hydrolytic stability failure may occur long before the first patently visible signs of degradation of the plastic.

One of the earliest detectable signs of plastic degradation is a change in the hardness. Thus, a simple and accurate means for measuring the hardness of plastic films can be used not only experimentally to test the hydrolytic stability of different plastics under different environmental conditions bu to monitor plastic coatings actually in use thereby to predict possible plastic failure before it occurs.

The major difficulties in testing the hardness of plastic films all relate to the fact that indentation must be extremely small in order not to penetrate the film. For a typical film of about 5/1000ths of an inch, the typical indentation should not be greater than 5/1000th of an inch, that is, penetration of the film to the substrate beneath must not occur. Thus, factors such as friction and small amounts of angular deflection of the indenter which might go unnoticed in testing a bulk material using indentations fifty to a hundred times as great, become a major source of error in measuring indentations on the order of 1/1000th of an inch.

Another important factor in measuring the hardness of plastics is "elastic recovery" — that is, the tendency for a material deformed under application of a force to rebound toward its original shape when the force is removed. Plastics demonstrate a much higher degree of "elastic recovery" than do metals and ceramics. Again, the factor of elastic recovery plays a much larger role in thin film testing than in testing bulk plastics. Thus, conventional methods of measuring indentations such as removing the indenter and inspecting the size of the indentation with a microscope or other optical device cannot be used for testing thin film plastics.

OBJECTS OF INVENTION

Accordingly, it is the primary object of this invention to provide a method and apparatus for testing the hardness of thin film plastics.

It is another object of this invention to provide a thin film hardness testing apparatus which is easily portable and rugged.

It is also an object of this invention to provide an apparatus for testing the hardness of thin film plastics which permis accurate, reproducible indentation readings to be made although the size of the indentation is extremely small.

SUMMARY OF INVENTION

In accordance with this invention, a method and apparatus have now been found which permit the hardness of thin film plastic films, ranging in thickness from about 1/100th–⅛th inch, to be measured quickly, easily and accurately. The basic apparatus comprises a platform for the sample to be tested, an indenter consisting of a straight vertically-placed shaft pointed on the lower end, a weight for applying a driving force to the indenter, and a dial gauge directly connected to the indenter to measure the vertical displacement of the indenter when the weight is applied.

DESCRIPTION OF PREFERRED EMBODIMENT

Figures 1, 3:
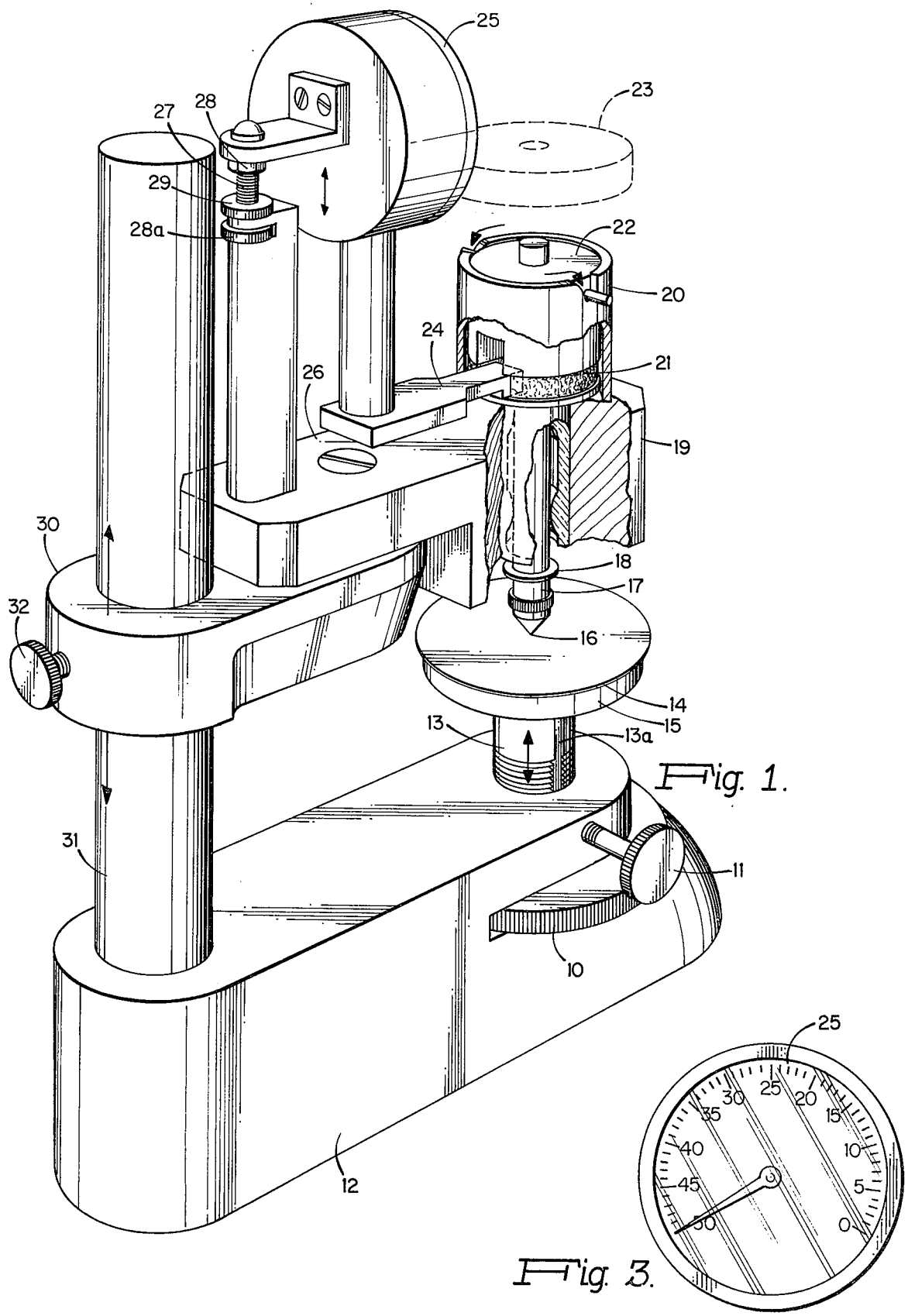
FIG. 1 is a partially cut-away perspective side view of the apparatus of the invention.
FIG. 3 illustrates the dial indicator.

Referring more particularly to the drawings, in FIG. 1 mounted in stand base 12 is internally-threaded adjustment dial 10 which mates with externally-threaded shaft 13 and thereby permits vertical movement of table 15 to bring sample 14, positioned thereon, to the bottom of indenter 16. Guide pin 11 is provided to ride in vertical groove 13a and, by tightening, to lock table 15 below indenter 16. Indenter 16 is screwed to shaft 17 whose travel is limited by washer 18. 19 is a bearing case with internal blushing for maintaining the indenter shaft in vertically-movable orientation. Weight retainer 20 contains a shock absorber 21, usually a flexible washer, which seats over the head of shaft 17. Weight 22 is normally used in hardness tests while weight 23, an auxilliary weight, is used only as required. Extension arm 24 is connected to dial indicator 25 on one end and rests on top of shaft 17 at the other end. The dial indicator is suitably mounted on stand 26 which is in turn connected to bearing case 19. Screw 27 having a button head and fixed nut 28 and holding dial indicator 25 travels through stand 26 by means of adjusting nut 28a and locks in position with locknut 29. Major adjustments are made by sliding stand support 30 up or down along shaft 31 using knob 32 to lock it in place.

Figure 2:
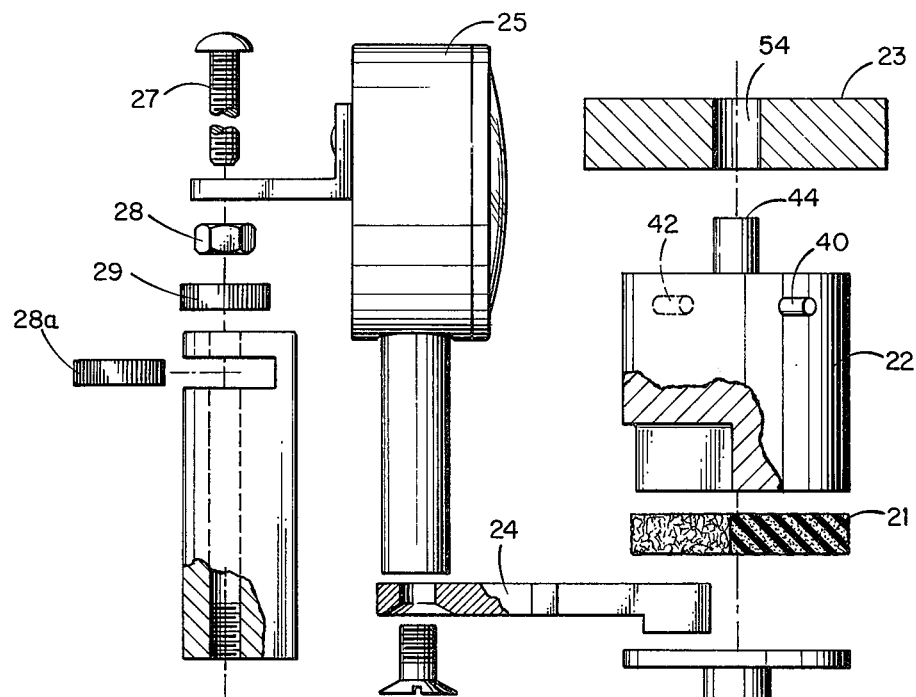
FIG. 2 is a schematic side view of the various components of the apparatus.
Figure 2:
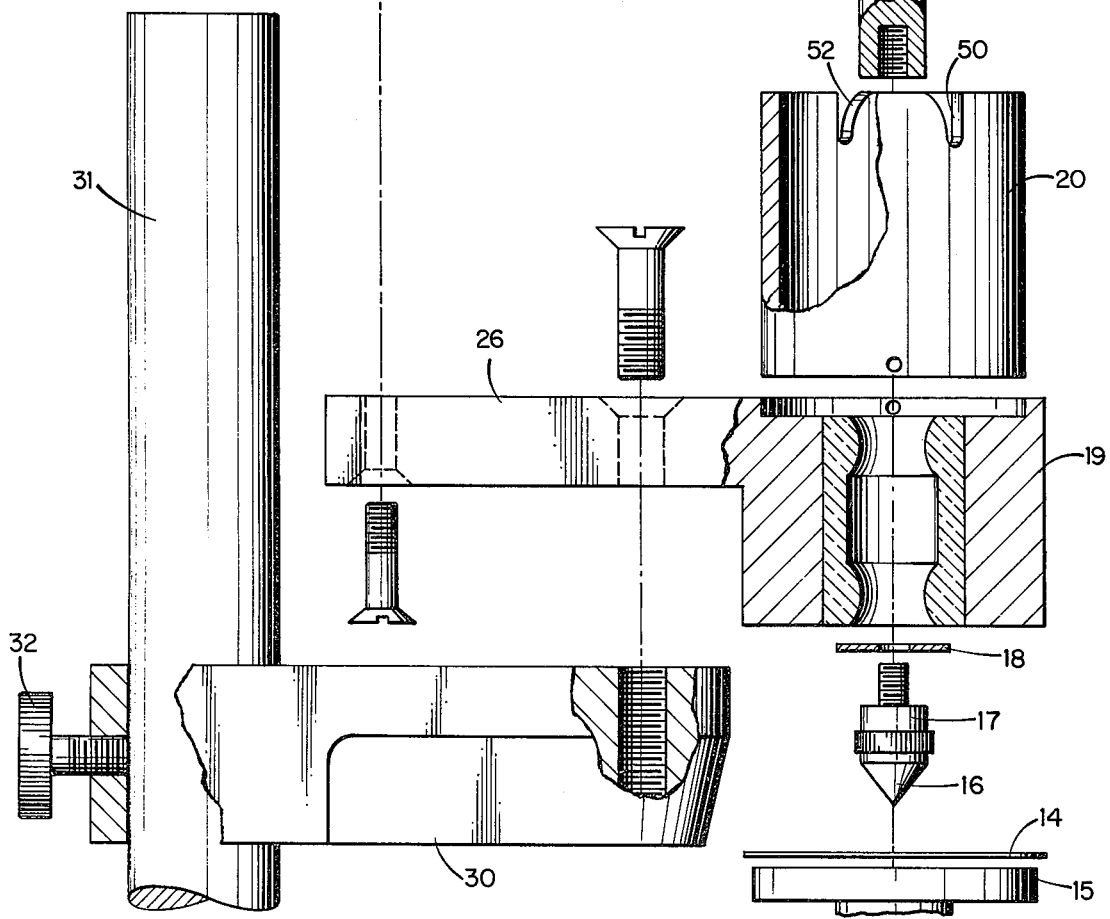

FIG. 2 illustrates more particularly the various parts of the apparatus of this invention and their respective spatial relationships. The numbering corresponds with FIG. 1. The side protrusions 40 and 42 of the weight 22 and the corresponding asymmetrically notched portions 50 and 52 of the weight retainer 20 are more clearly seen. Also seen is a top portion 44 of weight 22 designed to accommodate a hole or recess 54 in auxiliary weight 23.

FIG. 3 illustrates the face of the dial gauge.

The various parts of the apparatus should meet certain general standards for purposes of this invention.

The specification for the dial indicator are as follows: (1) it should be shockproof; (2) it should be almost frictionless; (3) there should be no backlash; (4) a force of about 10 grams should be sufficient to move the pointer about halfway across the dial face; (5) the dial should preferably be inscribed with graduations of 0–50 counterclockwise corresponding to a maximum displacement of 0.0050 in. of the indenter and the dial should be calibrated every 0.0001 in. and numbered at every fifth graduation, i.e. every 0.0005 in.

The specifications for the indenter call for a hardened and polished steel shaft, precision-made to slide in a ball bushing. The indenter point has a diamond tip and, in a preferred embodiment (not illustrated), is ground to a 60° angular point. The indenter should be able to travel a distance of 0.010 in. without penetrating the surface of a thin film telfon tape.

The specification for weight is a 50 gram chrome-plated steel weight. It should be made to engage and disengage in a cammed retainer whose inside is teflon-coated to reduce friction. An auxiliary weight of 60 grams is also provided to sit on top of the 50 gram weight. It is also possible to employ for the weights sealed plastic containers of mercury or tungsten weights having the appropriate weight to obtain a greater weight/mass ratio. The size of the weights is not crucial, however, and may be varied depending on the hardness of the film to be tested.

The assembled testing apparatus should itself meet the following specifications in order to measure the hardness of films as thin as 0.002 in.: (1) all motions of the device should be virtually frictionless; (2) the total applied weight should not exceed 150 grams; and, (3) the indenter should have a small radius of about 0.001 in.

EXAMPLE

The purpose of this example was to demonstrate the accuracy and reproducibility of the results in measuring the hardness of a plastic film deposited on a metal surface and having a thickness of about 0.005 in.

The test specimen was placed on the sample platform with the plastic coated surface face-up. With a 25 gram weight in the "up" position on the top of the weight retainer, the platform was raised by turning the adjusting knob until the surface of the specimen just contacted the bottom of the indenter as indicated by movement of the pointer on the dial gauge. The dial gauge was then calibrated to the "O"-position.

The weight was then "dropped" by turning the weight until the side protrusions were just at the beginning of the gradual slides in the asymmetrically notched portions of the weight retainer. A flexible washer was used to cushion the shock of the weight striking the top of the indenter shaft. After the weight came to rest, the indenter shaft was "tapped" lightly until no further change was indicated on the dial gauge to insure no friction and backlash of the indenter. (This "tapping" will not be required for precision-made instruments having jeweled bearings in accordance with this invention.) In two successive tests on the same sample in the above manner, the following results were obtained:

| Test No. | Dial Gauge Reading — inches |
|---|---|
| 1 | 0.00080 |
| 2 | 0.00075 |

Thus it can be seen that the method and apparatus permits simple and reproducible hardness tests on thin plastic films.

For even greater accuracy, it will be appreciated that the instrument of this invention may employ jeweled bearings and an electronic device instead of the simple mechanical dial gauge.

Having thus described the invention, what is claimed is:

1. An apparatus for testing the hardness of thin plastic films having a thickness of about 1/1000–1/8 inch comprising in combination:
   a. horizontal sample platform means for holding a sample to be tested together with means for limited vertical movement of said sample platform means;
   b. indenter means comprising a vertical shaft having a precision pointed indenter fixed to the lower end of said shaft together with horizontal weight platform means attached to said shaft for supporting a weight;
   c. almost-frictionless bearing and washer means for supporting said indenter means in a vertical position above said sample platform means and permitting limited vertical movement of said indenter means so as to bring the tip of said pointed indenter into contact with the top of said sample platform while restraining said indenter means from any angular deviation from vertical;
   d. weight means supported vertically above said weight platform means and capable of being applied to said indenter means by resting freely on said weight platform means wherein said weight has lateral protrusions and slides within a vertical guide tube which is notched to accommodate the said protrusions and additionally comprising a flexible washer as a shock absorber at the bottom of said guide tube and sitting on top of said indenter shaft; and,
   e. dial indicator means mechanically connected to said indenter means for determining when the sample is in contact with said indenter means before said weight means is applied and for determining the vertical displacement of said indenter means after said weight means is applied to said indenter means.

2. The apparatus of claim 1 wherein the pointed lower end of said indenter shaft has a radius of about 0.001 in.

3. The apparatus of claim 1 wherein said indenter shaft is a polished steel shaft with a diamond tip and slides in a ball bushing.

4. The apparatus of claim 1 wherein said guide tube is asymmetrically notched such that one side of each notch gradually slopes toward the bottom of the notch.

5. The apparatus of claim 1 wherein said dial gauge is graduated to record a vertical displacement of said indenter shaft of between 0.0001 and 0.0050 in.

6. A method for testing the hardness of thin plastic films having a thickness of about 1/1000–1/8 inch comprising the following steps:
 a. positioning a sample to be tested on a horizontal sample platform which is capable of limited vertical movement directly beneath a vertical shaft having a precision pointed indenter fixed to its lower end;
 b. elevating said sample platform until the top surface of said sample contacts the lower tip of said pointed indenter as determined by a dial gauge mechanically connected to said shaft, the indenter shaft being supported by almost-frictionless bearing and washer means permitting limited vertical movement while restraining said shaft against any angular deviation from vertical;
 c. applying a weight not exceeding about 150 grams to said indenter and shaft by freely resting said weight on a horizontal weight platform fixed to said indenter shaft, said weight being of such a size that the indenter and shaft are vertically displaced so as to partially penetrate said sample; and
 d. measuring the resulting vertical displacement of said shaft and indenter by means of said dial gauge mechanically connected to said shaft.

7. A method for testing the hardness of thin plastic films having a thickness of about 1/1000-1/8 inch comprising the following steps:
 a. positioning a sample to be tested on a horizonal sample platform which is capable of limited vertical movement directly beneath a vertical shaft having a precision pointed indenter fixed to its lower end;
 b. elevating said sample platform until the top surface of said sample contacts the lower tip of said pointed indenter as determined by a dial gauge mechanically connected to said shaft, the indenter shaft being supported by almost-frictionless bearing and washer means permitting limited vertical movement while restraining said shaft against any angular deviation from vertical;
 c. applying a weight having lateral protrusions to said indenter and shaft by resting said weight on top of an asymmetrically notched vertical guide tube communicating with weight platform means fixed to said indenter shaft and turning said weight until said protrusions begin to slide by gravity into said asymmetric notches, said weight being of such a size that the indenter and shaft are vertically displaced so as to partially penetrate said sample; and,
 d. measuring the resulting vertical displacement of said shaft and indenter by means of said dial gauge mechanically connected to said shaft.

* * * * *